United States Patent
De Cock

(10) Patent No.: US 10,886,019 B2
(45) Date of Patent: Jan. 5, 2021

(54) MEDICAL IMAGE ORIENTATION

(71) Applicant: KONINKLIJKE PHILIPS N.V., Eindhoven (NL)

(72) Inventor: Rudolfus Maria De Cock, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 176 days.

(21) Appl. No.: 16/086,628

(22) PCT Filed: Mar. 15, 2017

(86) PCT No.: PCT/EP2017/056047
§ 371 (c)(1),
(2) Date: Sep. 20, 2018

(87) PCT Pub. No.: WO2017/162491
PCT Pub. Date: Sep. 28, 2017

(65) Prior Publication Data
US 2019/0043612 A1    Feb. 7, 2019

(30) Foreign Application Priority Data
Mar. 22, 2016    (EP) .................................. 16161666

(51) Int. Cl.
G09G 5/00    (2006.01)
G16H 30/40    (2018.01)
G16H 40/63    (2018.01)
G06F 19/00    (2018.01)

(52) U.S. Cl.
CPC .......... *G16H 30/40* (2018.01); *G06F 19/321* (2013.01); *G16H 40/63* (2018.01)

(58) Field of Classification Search
CPC ....... G16H 30/40; G16H 40/63; G06F 19/321
See application file for complete search history.

(56) References Cited

U.S. PATENT DOCUMENTS

| 2009/0052761 A1 | 2/2009 | Atzinger |
| 2009/0310847 A1 | 12/2009 | Matsuzaki |
| 2013/0034280 A1* | 2/2013 | Bernhardt .............. A61B 6/464 382/128 |

(Continued)

FOREIGN PATENT DOCUMENTS

| JP | 2005013490 A | 1/2005 |
| WO | 2009119691 A1 | 10/2009 |

OTHER PUBLICATIONS

Wang, Lejing et al "Closed-Form Inverse Kinematics for Interventional C-Arm X-Ray Imaging with Six Degrees of Freedom: Modeling and Application", IEEE Transactions on Medical Image, vol. 31, No. 5, May 2012 pp. 1086-1099.

(Continued)

*Primary Examiner* — Charles Tseng

(57) ABSTRACT

Patient imaging systems suffer from the disadvantage that it is not clear to a medical professional using such systems which image view is the correct way around relative to a patient's body during a medical intervention. The present invention proposes automatically to adjust a display transformation applied to medical image data, based on an orientation of the patient imaging system received, for example, from a digital compass attached to the patient imaging system.

11 Claims, 6 Drawing Sheets

(56) References Cited

U.S. PATENT DOCUMENTS

2018/0055469 A1* 3/2018 Nam .................. A61B 6/504

OTHER PUBLICATIONS

Wolff, Thomas et al "C-Arm Angle Measurement with Accelerometer for Brachytherapy: an Accuracy Study", International Journal of Computer Assisted Radiology and Surgery, vol. 9, No. 1, Jul. 2013, pp. 137-144.

* cited by examiner

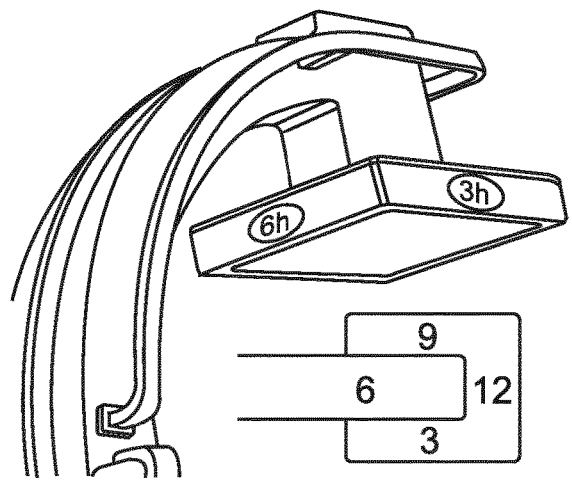
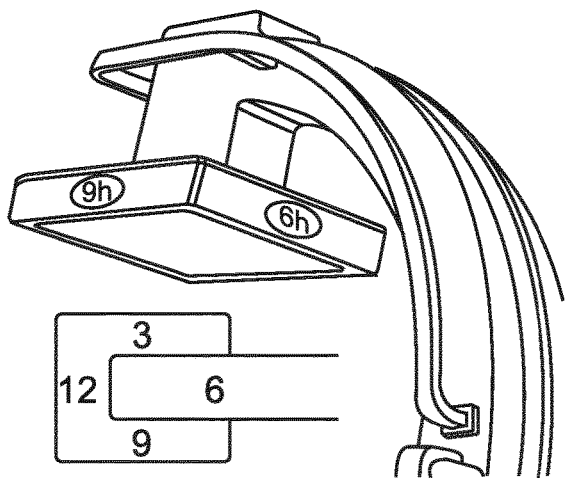
Fig. 4a    Fig. 4b
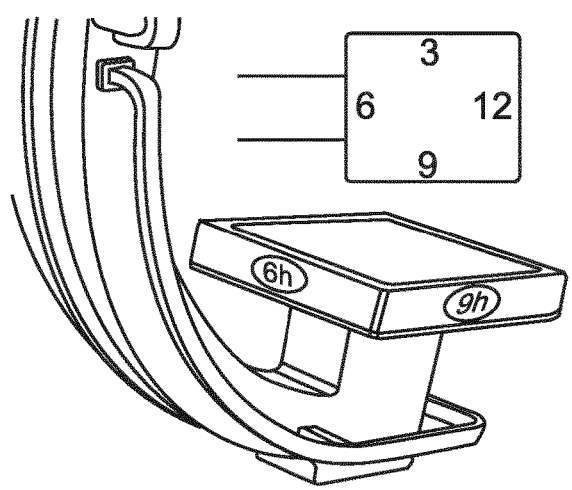
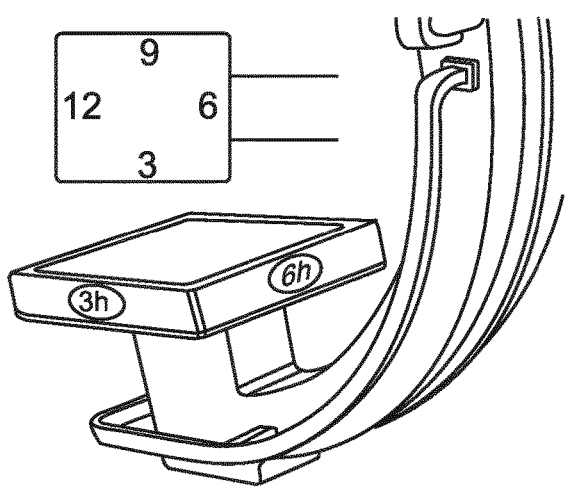
Fig. 4c    Fig. 4d

MEDICAL IMAGE ORIENTATION

CROSS-REFERENCE TO PRIOR APPLICATIONS

This application is the U.S. National Phase application under 35 U.S.C. § 371 of International Application No. PCT/EP2017/056047, filed on Mar. 15, 2017, which claims the benefit of European Patent Application No. 16161666.9, filed on Mar. 22, 2016. These applications are hereby incorporated by reference herein.

FIELD OF THE INVENTION

This invention relates to a medical imaging apparatus, a medical imaging method, a medical imaging system, a computer program element, and a computer-readable medium. More particularly, this invention relates to an approach for adjusting a display orientation of a medical imaging display.

BACKGROUND OF THE INVENTION

In a medical X-ray laboratory, a trend is towards providing display equipment as separately movable items. This enables medical staff to position X-ray imaging equipment in an ergonomically efficient manner. For example, a display monitor could be positioned on an opposite side of a patient to a patient imaging arrangement. At different stages of a medical intervention, there is often a requirement to move the C-arm imaging equipment, and thus a need to move the display screen as well.

Identifying the correct orientation of, for example, an X-ray image, when a stand-alone display monitor and a stand-alone C-arm imaging system are moved into different positions around a patient during an intervention can present a challenge. Conventionally, a medical professional will attempt to identify the correct orientation of the X-ray display using the X-ray image itself. However, this requires the patient imaging arrangement to be emitting X-ray radiation. Thus, conventionally, a patient can be exposed to short bursts of X-ray radiation, which are not useful for diagnostic purposes.

US 2009/0052761 concerns a system designed to display both digital fluoroscopy radiographic sequences, and conventional radiographic images, and to orientate the sequences and images. However, medical imaging display systems can be further improved.

SUMMARY OF THE INVENTION

It would, thus, be advantageous to have a technique for providing an improved medical imaging orientation technique.

The object of the present invention is solved by the subject-matter of the independent claims, wherein further embodiments are incorporated in the dependent claims.

These, and other aspects of the present invention will become apparent from, and be elucidated with reference to, the embodiments described hereinafter.

According to a first aspect of the invention, there is provided a medical imaging apparatus. The medical imaging apparatus comprises: an imaging interface configured to receive medical image data from an image detector on a patient imaging arrangement, an orientation information interface configured to receive orientation information of the patient imaging arrangement, and a processing unit.

The processing unit is configured to determine a display transformation of the medical image data based on the orientation information, to transform the medical image data from the patient imaging arrangement using the display transformation, thus providing transformed medical image data, and to output the transformed medical image data. Accordingly, orientation information of a patient imaging arrangement, such as a patient imaging arrangement, may be used automatically to transform the orientation of medical image data received from the patient imaging arrangement onto a display. This means that re-orientations of the patient imaging arrangement will also change the orientation of the medical image as it is displayed on a display connected to the imaging interface of the medical imaging apparatus. Therefore, when the patient imaging arrangement is moved around in an X-ray imaging treatment suite, for example, a medical professional does not need to expose a patient to X-ray radiation which is not used for clinical (i.e. diagnostic) purposes.

A display unit may be connected to the output of the medical imaging apparatus. The display unit is able to display medical image data captured by the image detector of the patient imaging arrangement at the correct orientation, using the orientation information received from the patient imaging arrangement.

According to an embodiment of the first aspect, the orientation information received by the orientation information interface comprises inclination and/or rotation signals from the patient imaging arrangement.

Accordingly, the display transformation may be determined based upon orientation information received from a patient imaging arrangement. Patient imaging arrangements typically have an electronic control system that is able to output inclination and rotation signals for use by patient imaging equipment. Thus, the medical imaging apparatus may provide a display transformation based on the inclination and rotation of the patient imaging arrangement.

According to an embodiment of the first aspect, the orientation information received by the orientation information interface comprises video information of the patient imaging arrangement.

In this embodiment, an external video camera is provided which monitors the location of the patient imaging arrangement. The inclination, and rotation of the C-arm gantry, and the azimuth angle of the dolly of the patient imaging arrangement, can be derived using video processing algorithms applied to the video information obtained by the video camera.

According to an embodiment of the first aspect, the orientation information interface is further configured to receive video information of a patient's alignment in the patient imaging arrangement from a video camera. The processing unit is further configured to process the video information to determine an offset measure of the patient from a principal patient axis relative to an alignment of the patient imaging arrangement. The processing unit is configured to determine the display transformation of the medical imaging data based additionally on the determined offset measure.

Alignment of a patient in a patient imaging arrangement (such as a C-arm imaging system) can also affect the alignment of the displayed medical imaging data. A misalignment of a patient in the imaging region of the patient imaging arrangement implies a further need to alter the display transformation of the medical image data. According to this embodiment, the video camera additionally calculates the offset of the patient's alignment in the patient imaging arrangement, and corrects the display transformation to remove the misalignment.

According to an embodiment of the first aspect, the medical imaging apparatus further comprises a user interface. The user interface is further configured to receive a manual image correction signal, enabling an input of a manual image correction factor by a user. The processing unit is further configured to determine the display transformation by combining the manual image correction factor with the orientation information.

Accordingly, a fail-safe approach is provided whereby a medical professional may manually adjust the automatically determined orientation information using an interface of the medical imaging apparatus.

According to an embodiment of the first aspect, the display transformation is one, or any combination of: (i) a clockwise or counter-clockwise rotation of 90 degrees, (ii) a clockwise or counter-clockwise rotation of 180 degrees, (iii), a clockwise or counter-clockwise rotation of 270 degrees, (iv) a mirror transformation applied around a horizontal and/or vertical line of symmetry, (v) an output of an orientation transfer function. Accordingly, the medical imaging apparatus according to this embodiment can apply a wide range of display transformations to the medical image data for the convenience of a medical professional using the patient imaging arrangement.

According to a second aspect of the invention, a method for adjusting a display orientation of a medical imaging display is provided. The method comprises:
 a) receiving orientation information of a patient imaging arrangement;
 b) receiving medical image data from an image detector on the patient imaging arrangement;
 c) determining a display transformation of the medical image data based on the orientation information;
 d) transforming the medical image data from the patient imaging arrangement using the display transformation, thus providing a transformed medical image and/or a transformed medical image sequence; and
 e) displaying the transformed medical image data.

Accordingly, a method according to the second aspect enables the automatic re-orientation of medical image data for the convenience of a medical professional. According to an embodiment of the second aspect, the orientation information received by the orientation information interface comprises inclination and/or rotation signals from the patient imaging arrangement.

According to an embodiment of the second aspect, the method further comprises:
 a1) receiving video information of the patient imaging arrangement from a video camera, and wherein d) further comprises:
 d1) determining an offset measure of a principal patient axis, relative to an alignment of the patient imaging arrangement using the video signal, and
 wherein in c), the display transformation of the medical image data is based additionally on the determined offset of the principal patient axis relative to the imaging axis.

According to an embodiment of the second aspect, the method further comprises:
 a2) receiving, from a user interface, a manual image correction signal, enabling a manual input of a manual image correction factor by a user; and
 wherein in e), the determination of the display transformation further comprises combining the manual image correction angle with the orientation information.

According to a third aspect of the invention, a medical imaging system is provided. The system comprises
 a patient imaging arrangement;
 a display unit; and
 a medical imaging apparatus as discussed according to the first aspect or its embodiments.

The patient imaging arrangement comprises an orientation sensor configured to provide orientation information to the medical imaging apparatus, and an image detector configured to provide medical image data to the medical imaging apparatus.

The display unit is configured to display transformed medical image data output by the medical imaging apparatus.

Accordingly, as a patient imaging arrangement and a display unit are moved around a patient imaging laboratory (such as a catheterization laboratory), an ergonomically acceptable display orientation is automatically provided based on the orientation of the patient imaging arrangement.

According to an embodiment of the third aspect, the orientation sensor is a dual-axis or a triple axis accelerometer.

Therefore, a wide range of motion changes can be tracked. The rotation of the patient imaging arrangement, and/or its translation through a patient imaging laboratory, may be tracked, for example.

According to an embodiment of the third aspect, the medical imaging system comprises a video camera configured to provide video information of the location of the patient imaging arrangement to the medical imaging apparatus.

Therefore, the relative position of a patient imaging system and a display unit may be derived through visual means.

According to a fourth aspect of the invention, there is provided a computer program element for controlling a medical imaging apparatus according to the first aspect or its embodiments, which, when the computer program element is executed by a processing unit, is adapted to perform the steps outlined in the second aspect, or one of its embodiments. According to a fifth aspect of the invention, there is provided a computer-readable medium having stored the computer program element of the fourth aspect.

In the following specification, the term "patient imaging arrangement" may include a C-arm X-ray imaging arrangement, arranged to be movable on a dolly (or trolley). It will be appreciated, though, that a wide range of patient imaging arrangements may benefit from the technique described herein.

In the following specification, the term "orientation information" refers to information enabling the identification of the present disposition of a patient imaging arrangement. The disposition may include, for example, the change in rotation and/or inclination of a C-arm gantry, or a horizontal translation of a patient imaging arrangement. The orientation information may include the orientation of a patient in the patient imaging arrangement.

A patient imaging arrangement, such as a C-arm imaging arrangement, is typically disposed on a dolly, which is a movable trolley. A two-axis or three-axis accelerometer may be disposed on the dolly itself, or on an element of the C-arm. Thus, rotation information may be provided as orientation information. Optionally, inclination and rotation signals are provided from the electronic drive system of the patient imaging arrangement. Optionally, orientation information is provided as video information of the region of operation of a patient imaging arrangement. The video information is optionally post-processed to extract C-arm inclination and rotation signals, or the state of rotation or translation of the C-arm dolly, or the patient position. Therefore, it will be appreciated that many different types of orientation information may be used in the present aspects.

Thus, it is a basic idea of the invention to use orientation information of a patient imaging arrangement to transform the orientation of display information from the patient imaging arrangement. This enables a more ergonomically appropriate display of medical image data from the patient imaging arrangement.

BRIEF DESCRIPTION OF THE DRAWINGS

Exemplary embodiments will be described with reference to the following drawings:

FIGS. 4a) to 4d) show an orientation tracking convention of a patient imaging arrangement (a C-arm system) from various attitudes of the patient imaging arrangement.

DETAILED DESCRIPTION OF EMBODIMENTS

Patient imaging using a mobile patient imaging arrangement can present problems to a medical professional, because it is often difficult for a medical professional to identify the correct orientation of a patient imaging display, relative to a patient, from the display itself. Typically, patient imaging arrangements are moved around on a dolly (a mobile carriage configured to hold the patient imaging arrangement), often within the same medical procedure, to achieve a more convenient view for a specific part of the medical procedure. Therefore, time is spent during an imaging procedure, or an interventional procedure, manually adjusting a patient imaging display to ensure good alignment of the image displayed to a medical professional.

Figure 1:
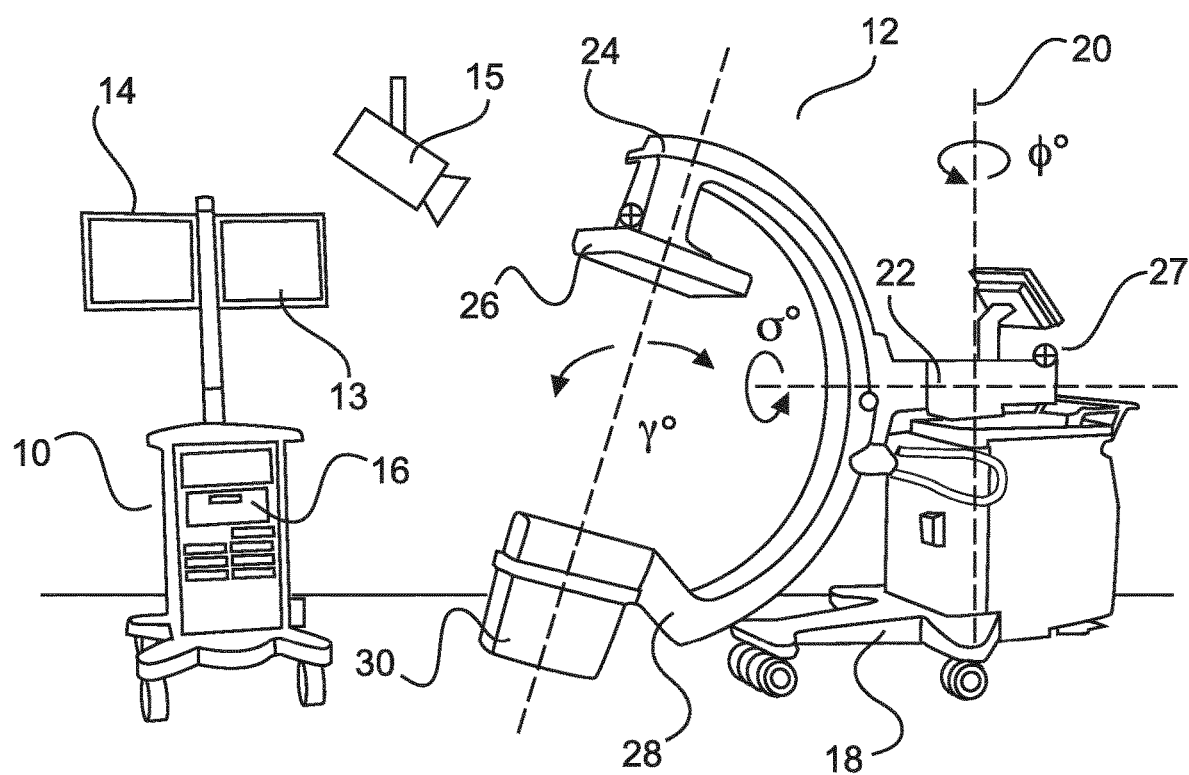
FIG. 1 shows a general view of a C-arm imaging laboratory.

FIG. 1 shows a C-arm X-ray imaging system, which will subsequently be described. A C-arm X-ray imaging system is an example of a type of patient imaging arrangement which this description will focus on, although other types of mobile patient imaging arrangements exist, to which the technique to be described herein could advantageously be applied.

A C-arm X-ray imaging system is commonly used during interventional fluoroscopy. FIG. 1 shows a C-arm X-ray imaging system 10 is shown. The C-arm X-ray imaging system 10 comprises a C-arm imaging arrangement 12, a display unit 14, and a medical imaging apparatus 16. Although the medical imaging apparatus 16 is shown as comprised within the display unit, it will be appreciated that this unit can be placed in many places in the medical imaging suite.

In FIG. 1, the C-arm imaging arrangement 12 is supported on a dolly 18. The entire C-arm imaging arrangement 12 may be moved backwards and forwards, or rotated about a vertical axis 20 using the dolly 18. The C-arm imaging arrangement 12 may be rotated on the dolly 18 around a vertical axis 20 by a translation angle $\varphi°$.

An orbital drive means 22 supports a C-arm gantry 24 on the dolly 18. The orbital drive means 22 enables the C-arm gantry 24 to be repositionable along an extended arc segment of the C-arm gantry 24 by an inclination angle $\gamma°$.

The orbital drive means 22 also enables the C-arm gantry 24 to be repositionable in a rotational sense to the dolly 18 by a rotation angle $\sigma°$.

A first end 24 of the gantry supports an X-ray detector 26. A second end 28 of the C-arm gantry supports an X-ray source 30. A patient is positioned in-between the X-ray detector 26 and the X-ray source 30. Variation of the dolly angle $\varphi°$, the inclination angle $\gamma°$, and the rotation angle $\sigma°$ enables a significant range of views of a patient to be obtained during an interventional procedure. Horizontal translations of the position of the dolly 18 around a patient extend further the range of views of the patient that are possible.

A goal of radiographic imaging is to reduce the exposure of a patient to unnecessary doses of X-ray radiation. Some approaches focused on reducing the intensity of an X-ray source, or improving the sensitivity of an X-ray detector, and yet other approaches focused on improved image processing.

The alignment of a patient imaging system-using X-rays, such as the C-arm system 12 of FIG. 1, often occurs when the patient imaging system is operational. Changes of the orientation of the C-arm system 12 can cause confusing alterations in the orientation of an output image on a display unit 14, requiring manual re-orientation of the image on a display unit 14 whilst a patient is exposed to X-rays from the C-arm imaging arrangement.

According to the "ALARA" principle ("As Low As Reasonably Possible"), such X-ray exposures of negligible diagnostic utility should be minimized.

According to a first aspect of the invention, there is provided a medical imaging apparatus 32. The medical imaging apparatus 32 comprises: an imaging interface 34 configured to receive medical image data 36 from an image detector on a patient imaging arrangement, an orientation information interface 38 configured to receive orientation information 40 of the patient imaging arrangement, and a processing unit 42.

The processing unit 42 is configured to determine a display transformation of the medical image data 36 based on the orientation information 40, to transform the medical image data from the patient imaging arrangement using the display transformation, thus providing transformed medical image data 43, and to output the transformed medical image data 43.

Figure 2:
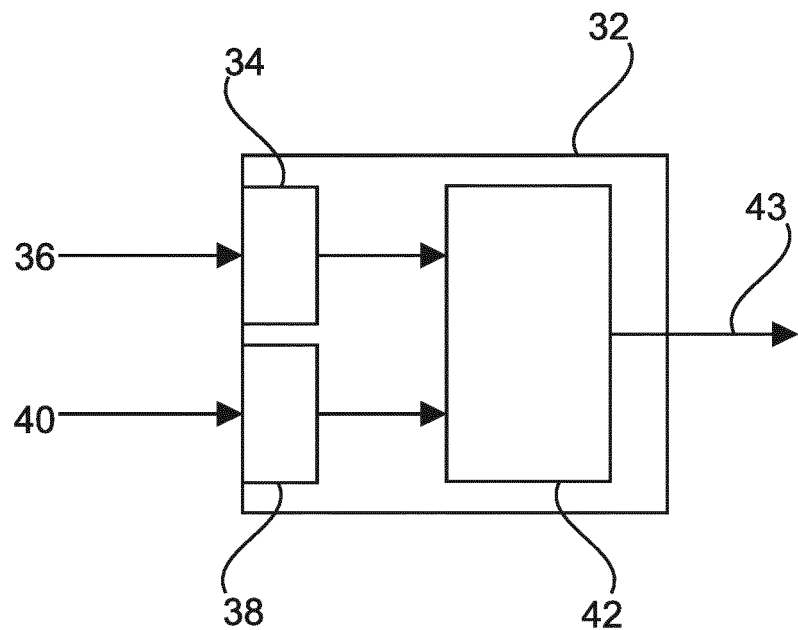
FIG. 2 shows a medical imaging apparatus according to the first aspect.

FIG. 2 illustrates a medical imaging apparatus 32 in accordance with the first aspect. The imaging interface 34 may be a common wired or wireless data transfer means (such as Ethernet or Wi-Fi™) capable of receiving data according to common medical imaging standards such as PACS. Signals from an X-ray detector of a C-arm imaging arrangement, for example, are received by the imaging interface 34, and typically contain still, or sequenced, X-ray image data. If medical image data is viewed in the format that it is at the orientation information interface directly, the orientation of the X-ray image on a display means will change as the C-arm imaging arrangement is inclined, rotated, or translated around a patient on the dolly 18.

The processing unit 42 is provided, for example, as a personal computer (PC), a microprocessor, a digital signal processor (DSP), a field programmable gate array (FPGA), or other means capable of processing data. The processing unit is configured to output transformed medical imaging data 43.

In operation, the processing unit receives orientation information 40 from the orientation information interface 38. The processing unit 42 compares the orientation information to an orientation display condition.

The processing unit 42 combines the medical image data 36 and the orientation information from the imaging interface 34 and the orientation information 38. As will be described subsequently, the processing unit 42 is configured to determine a display transformation of the medical image data 36 based on the orientation information. Having determined the display transformation, the processing unit 42 transforms medical image data using the display transformation, providing transformed medical image data. In other words, the processing unit 42 determines a logical condition of the orientation information, and chooses a display transformation appropriate to that logical condition.

As a simple example, if the angulation information φ degrees of the C-arm imaging dolly indicates that the C-arm dolly has been moved through an arc of 180 degrees, the medical image data may be offset at 180 degrees compared to the initial resting position of the dolly. Therefore, if the orientation information indicates that such a condition is present, the display transformation may be selected as a 180 degrees translation in the opposite direction to the direction of the dolly. In this way, the translation applied to the medical image data by the translation of the C-arm dolly can be reversed by selecting the appropriate display transformation.

In another simple example, the orientation display condition monitors whether the C-arm gantry is aligned so that the X-ray detector 26 is above a patient, or below a patient. If the processing unit 42 detects that the rotation of the C-arm gantry changes from a situation in which the X-ray detector 26 is below a patient to being above a patient, then the display transformation can, in this example, be chosen as a mirror transform. More sophisticated techniques for assessing the display transformation will be discussed subsequently.

Figure 3:
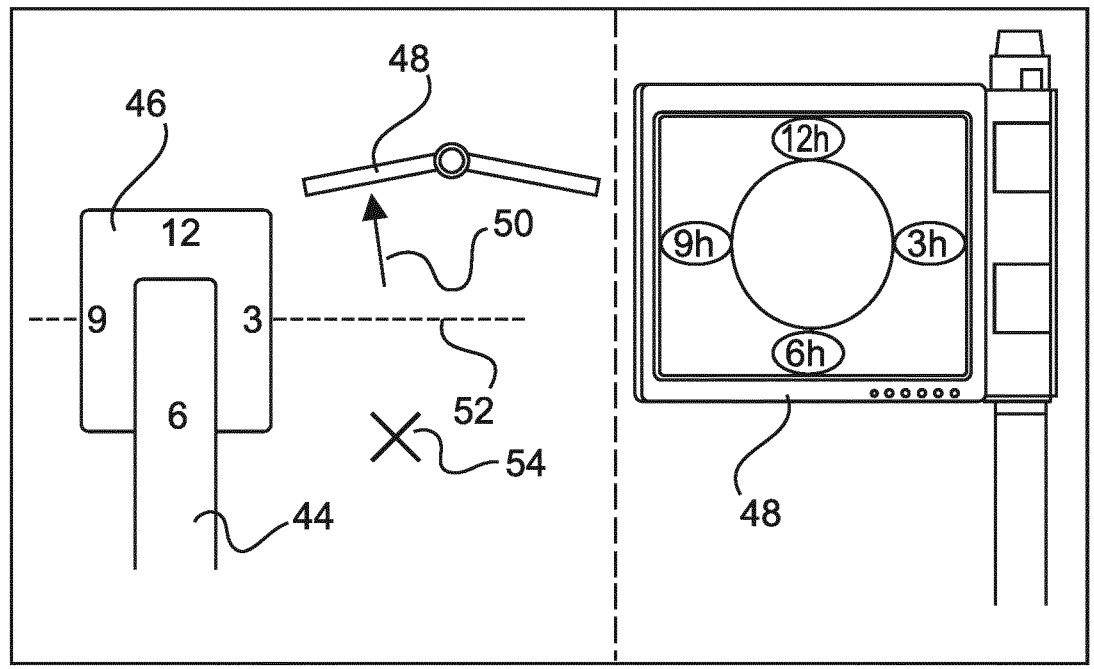
FIG. 3 shows a schematic layout of a medical imaging system.

FIG. 3 illustrates a schematic plan view of the X-ray detector end of a C-arm imaging arrangement 44, showing the X-ray detector head 46. A display arrangement 48 can be seen with an arrow 50 indicating a typical view direction of a medical professional. A dotted line 52 illustrates a principle patient axis of the system. The right-hand side of FIG. 3 illustrates a display apparatus 48 from a front view. A patient's spine would be aligned along this axis.

Therefore, it is seen that the illustrated 12 o'clock position of the X-ray detector head 46 is presented closest to the display arrangement 48. A section of the X-ray detector closest to the C-arm imaging arrangement gantry is shown at the bottom of the display arrangement 48 at the 6 o'clock position. In this example, the 9 o'clock position of the X-ray detector head 46 is in alignment with the left-hand side of the display arrangement, and the 3 o'clock position of the X-ray detector head 46 is in alignment with the 3 o'clock position of the display arrangement 48.

Optionally, the orientation information interface 38 is configured to receive data signals from orientation detecting devices. For example, the orientation information interface can optionally receive inclination γ° and rotation σ° information from a C-arm electronic stepper motor drive system.

Optionally, or in combination, the orientation information may comprise angulation signals obtained from an orientation sensor. The orientation sensor may, for example, be a digital compass 27 (a two-axis or a three-axis accelerometer) located on the body of the C-arm dolly, and/or the C-arm X-ray detector 26, and/or the C-arm X-ray source.

Optionally, the orientation information may be provided by a video camera 15 providing video information of the C-arm imaging arrangement. Video post-processing is performed on the video stream from the video camera 15, so that C-arm imaging arrangement inclination, rotation, and angulation signals can be provided to the orientation information interface 38.

FIG. 4*a*) shows a close-up view of an aspect of the C-arm gantry, showing the 6 o'clock and 3 o'clock sides.

FIG. 4*b*) shows a view of the C-arm imaging arrangement gantry from the opposite side to that in FIG. 4*a*), where the 9 o'clock and 6 o'clock faces are visible.

FIG. 4*c*) shows situations where the C-arm gantry has been completely rotated to enable the X-ray detector head to view the underside of a patient. Therefore, the 6 o'clock and 9 o'clock faces of the X-ray detector head are visible in FIG. 4*c*).

FIG. 4*d*) shows the C-arm imaging arrangement in the fully rotated position (as in FIG. 4*c*) with the 6 o'clock and 3 o'clock sides of the X-ray detector head visible. Thus, this notation convention will be used to explain the invention.

Optionally, the length axis (the principle patient axis) of the patient with respect to the X-ray detector head can be determined using a video camera above the patient, for example, located on the X-ray detector head. Optionally, the camera is an infra-red camera.

Figure 5A:
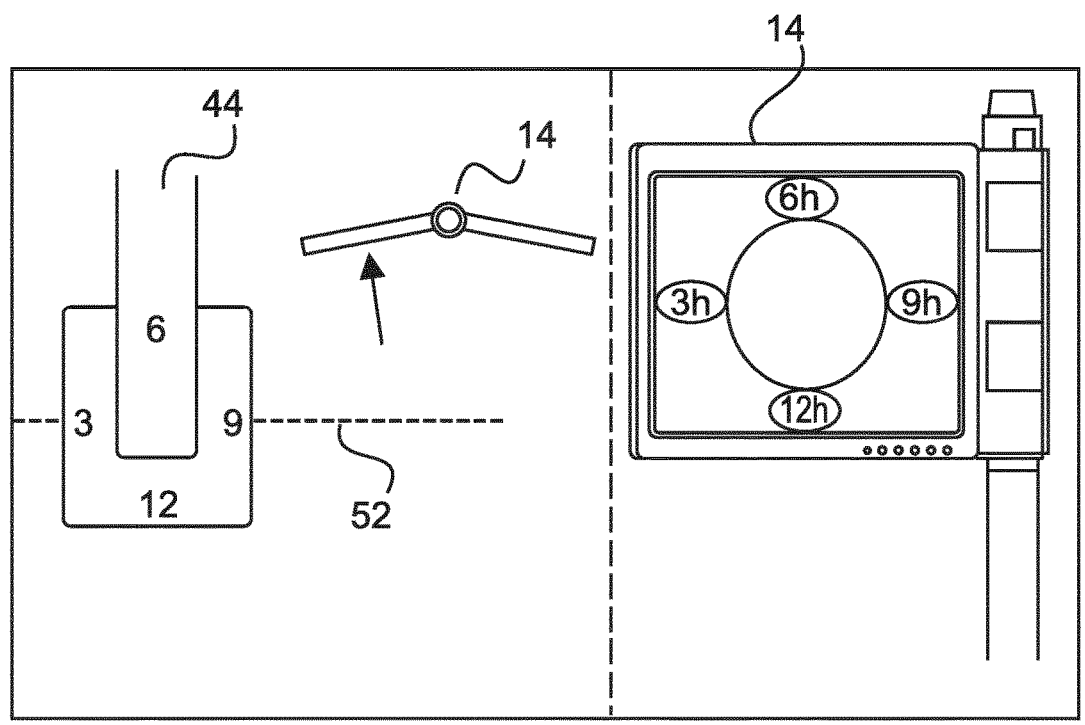
FIG. 5a) shows a display transformation of 180 degrees.

FIG. 5*a*) illustrates a use-case in which the display unit 14 is located on the same side of the patient as the C-arm imaging arrangement and gantry 44. In the situation illustrated in FIG. 5*a*), a display transformation comprising an image rotation of the medical image data of 180 degrees before display on the display arrangement 14.

Figure 5B:
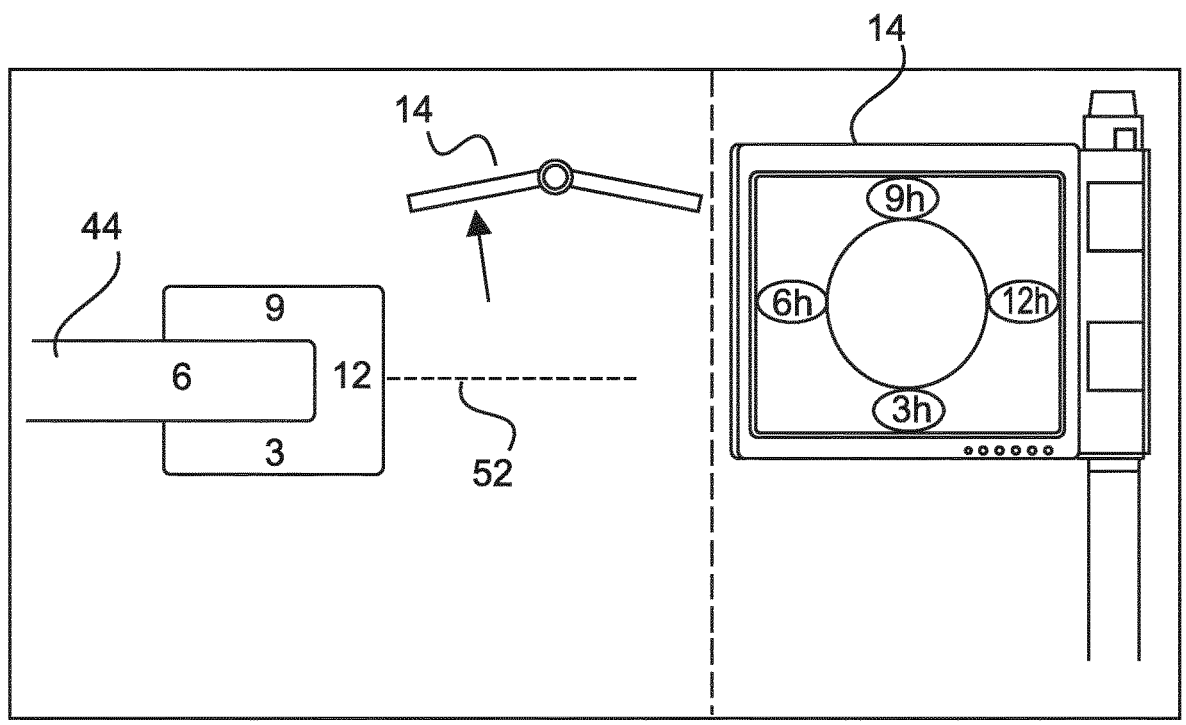
FIG. 5b) shows a display transformation of 90 degrees.

In FIG. 5*b*), the C-arm imaging arrangement has been positioned so that the C-arm gantry 44 is aligned in parallel with the principle patient axis 52. Therefore, in this case, a display transformation comprising an image rotation of 90 degrees to medical image data from the X-ray detector head of the C-arm imaging arrangement before display on the screen 14.

Figure 5C:
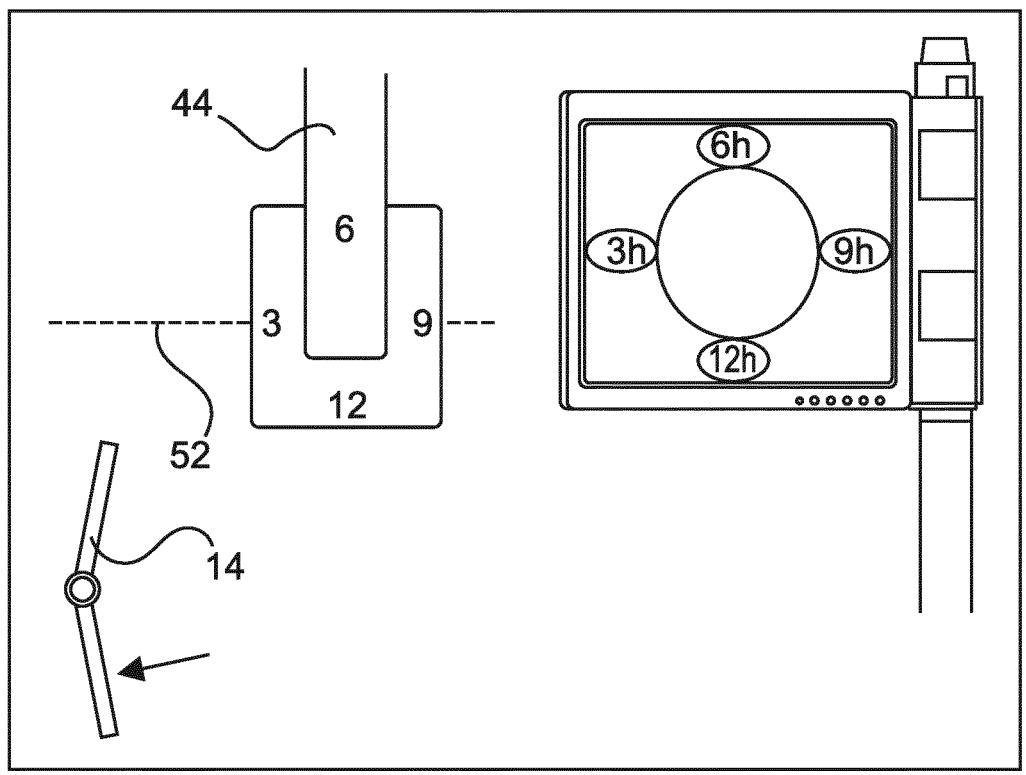
FIG. 5c) shows a display transformation of 180 degrees.

FIG. 5*c*) shows a situation where the display unit 14 is positioned to the bottom side of the principle patient axis 52, and the gantry 44 of the C-arm imaging arrangement is positioned perpendicularly to the principle patient axis 52. In this case, a display transformation comprising an image rotation of 180 degrees is performed by the medical imaging apparatus 32.

Figure 5D:
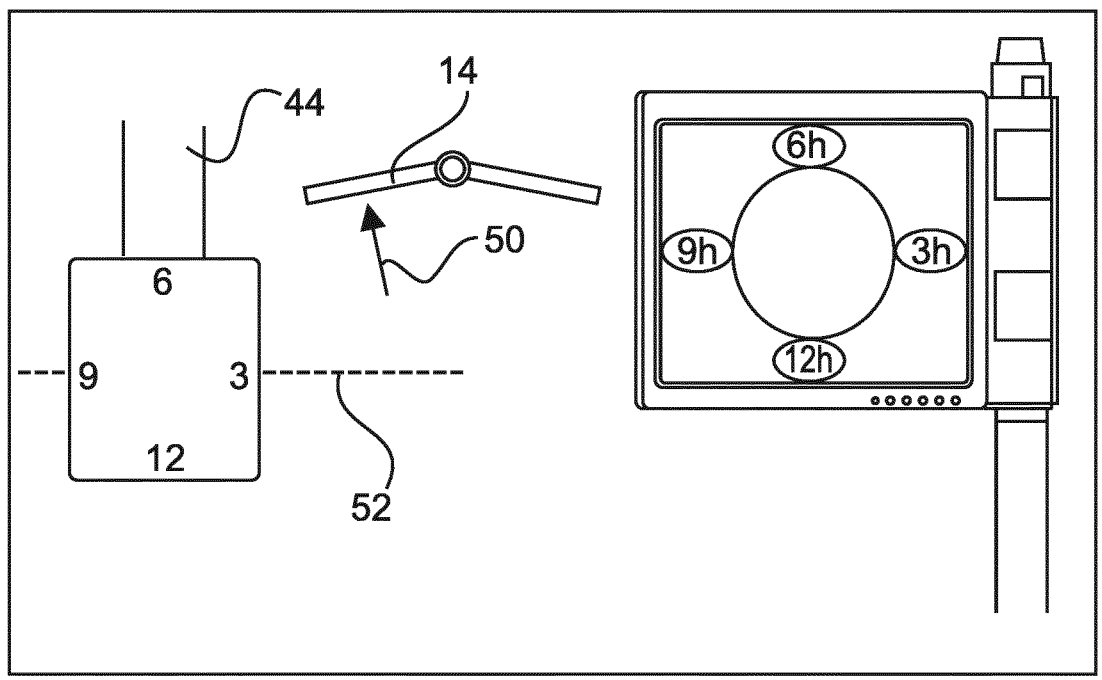
FIG. 5d) shows a display transformation comprising a rotation of 180 degrees, and a horizontal mirror effect.

FIG. 5*d*) illustrates a situation where the X-ray detector 26 of the C-arm imaging arrangement is positioned below the X-ray source 30. In this situation, the X-ray detector 26 observes the patient from the opposite side to the conventional side. Therefore, in FIG. 5*d*), a display transformation of an image rotation of 180 degrees, and a horizontal mirroring operation is performed by the medical imaging apparatus 32.

Figure 5E:
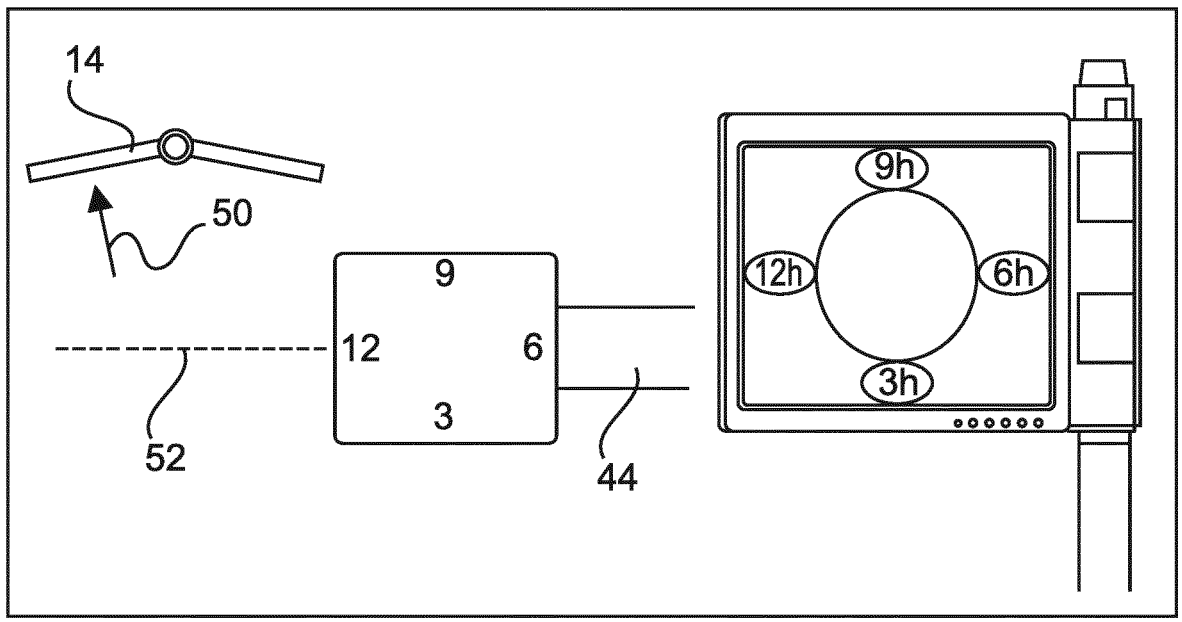
FIG. 5e) shows a display transformation comprising an image rotation of 90 degrees and a horizontal mirror effect.

FIG. 5*e*) illustrates a situation where the X-ray detector 26 is positioned below the X-ray tube 30. The display apparatus 14 is illustrated in parallel to the principle patient axis 52. The gantry of the C-arm imaging arrangement is positioned in parallel to the principle patient axis 52. In this case, an image rotation of 90 degrees and a horizontal mirroring operation is performed as the display transformation applied to the medical image data received from the C-arm imaging arrangement.

It will be appreciated that the correct image orientation cannot always be determined automatically. Optionally, the processing unit 42 may receive a manual update to combine with the display transformation. The manual update is applied by a user, for example, through a graphical user interface of the system, or by a hardware manual adjustment knob.

Optionally, the medical imaging apparatus 32 may be located inside a trolley holding the display unit 14 of a patient imaging arrangement 12, in which case connection of the display unit 14 to the medical imaging apparatus 32 is facilitated.

Optionally, the medical imaging apparatus 32 may be located on the patient imaging arrangement 12 (such as a C-arm imaging arrangement). In this case, the medical imaging apparatus 32 may transmit the transformed medical image data to the display unit 14 by wired or wireless communication.

Optionally, the medical imaging apparatus 32 may be located remotely from both the C-arm dolly 18 and the display unit 14 trolley, and instead be located in another part of the patient imaging laboratory. In this case, orientation information signals and imaging interface signals may be transmitted between the display unit and the C-arm imaging arrangement using a variety of wired and wireless communication techniques known to the person skilled in the art.

Figure 6:
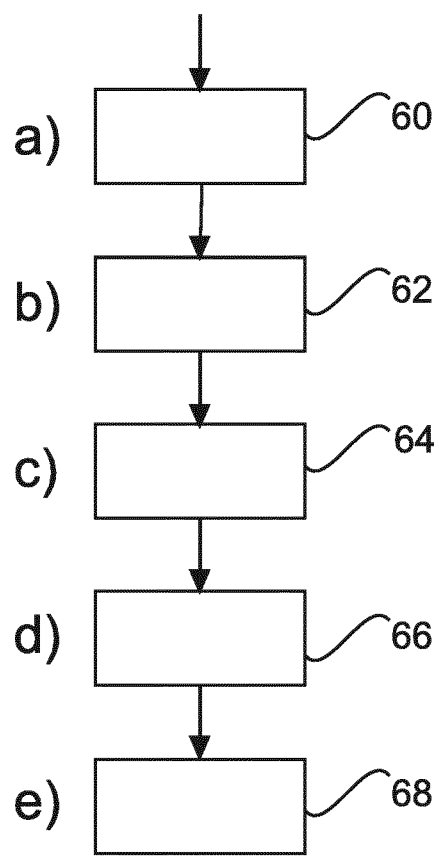
FIG. 6 shows a method for adjusting a display orientation of a medical imaging display according to the second aspect.

FIG. 6 illustrates the method according to the second aspect of the invention. According to the second aspect of the invention, a method for adjusting a display orientation of a medical imaging display is provided. The method comprises:
  a) receiving 60 orientation information 40 of a patient imaging arrangement;
  b) receiving 62 medical image data 36 from an image detector on the patient imaging arrangement;
  c) determining 64 a display transformation of the medical image data based on the orientation information;
  d) transforming 66 the medical image data from the patient imaging arrangement using the display transformation, thus providing a transformed medical image and/or a transformed medical image sequence; and
  e) displaying 68 the transformed medical image data 43.

Optionally, the method of the second aspect comprises in a), that the orientation information 40 received by the orientation information interface 38 comprises inclination and/or rotation signals from the patient imaging arrangement.

Optionally, the method of the second aspect further comprises:
  a1) receiving video information of the patient imaging arrangement from a video camera, and wherein d) further comprises:
  d1) determining an offset measure of a principal patient axis 52, relative to an alignment of the patient imaging arrangement using the video signal, and wherein in c), the display transformation of the medical image data is based additionally on the determined offset of the principal patient axis relative to the imaging axis.

Optionally, the method of the second aspect further comprises:
  a2) receiving, from a user interface 13, a manual image correction signal, enabling a manual input of a manual image correction factor by a user; and wherein in e), the determination of the display transformation further comprises combining the manual image correction angle with the orientation information.

According to a third aspect, a medical imaging system 12 is provided comprising:
  a patient imaging arrangement 24, 26, 28, 30;
  a display unit 14; and
  a medical imaging apparatus 16, 32 as discussed in the first aspect, or its embodiments.

The patient imaging arrangement comprises an orientation sensor 27 configured to provide orientation information to the medical imaging apparatus, and an image detector 26 configured to provide medical image data to the medical imaging apparatus 16, 32; and the display unit 14 is configured to display transformed medical image data output by the medical imaging apparatus.

FIG. 1 also illustrates a system according to the third aspect of the invention. FIG. 1 has already been described in the above part of the description in relation to the first aspect.

Optionally, the display unit 14 comprises a second orientation sensor. The second orientation sensor provides display unit angulation information, which is also comprised in the orientation information. According to this option, the processing unit 42 is configured to compute the display transformation using the display unit angulation information from the second orientation sensor, in addition to the orientation information from the orientation sensor 27 located on the patient imaging arrangement.

According to embodiments of the invention, display transformation information is provided wherein the display transformation is one, or any combination of: (i) a clockwise or counter-clockwise rotation of 90 degrees, (ii) a clockwise or counter-clockwise rotation of 180 degrees, (iii), a clockwise or counter-clockwise rotation of 270 degrees, (iv) a mirror transformation applied around a horizontal and/or vertical line of symmetry, (v) an output of an orientation transfer function.

The orientation transfer function discussed in (v) is a mapping between the orientation information, and the display transformation applied to the image from the patient imaging arrangement.

According to an embodiment, the orientation transfer function comprises a limit function. Therefore, an extreme movement at the boundary of the range of a two-dimensional or three-dimensional compass has a small effect on the display transformation, but a smaller movement in the middle of the range of the compass has a significant effect on the display transformation.

According to an embodiment, the orientation transfer function comprises hysteresis. Therefore, for example, a motion of the patient imaging equipment in a first direction will cause a commensurate change in the display transformation applied to the image from the patient imaging arrangement. However, a more extreme motion is required in a second direction to cause a commensurate change in the display transformation in an opposite direction.

According to an embodiment, the patient imaging arrangement is a C-arm X-ray imaging arrangement.

Optionally, according to one setting, if the orientation information indicates that the patient imaging arrangement (C-arm imaging arrangement) has changed through at an angle of least ninety degrees (clockwise or anticlockwise) then the display transformation information as an angle of least ninety degrees (anticlockwise or clockwise), respectively.

Optionally, according to another setting, if the orientation information indicates that the patient imaging arrangement (C-arm imaging arrangement) has changed through a particular angle, then the display transformation information is provided as a negative angle of at least the particular angle.

Optionally, according to another setting, if the orientation information indicates that the patient imaging arrangement (C-arm imaging arrangement) has changed through a particular angle, then the display transformation information is provided having a hysteresis, so that a larger opposite change must be made to the orientation of the patient imaging arrangement to obtain a commensurate negative change in the display transformation information.

Optionally, the display transformation information is provided as the output of a transfer function of the orientation information. For example, the display transformation information may be scaled as a linear function of the orientation information, or as a quadratic function of the orientation of the orientation information, or as a piecewise function of the orientation information.

It will be noted that the above-stated steps may also be executed in a different order. For example, the medical image data may be received from the image detector of a C-arm imaging arrangement before the orientation of the C-arm imaging is received.

In another aspect of the present invention, a computer program, or a computer program element, is provided that is characterized by being adapted to execute the method steps of the method of the second aspect, or its embodiments, as discussed according to one of the preceding embodiments, on an appropriate system.

The computer program element might therefore be stored on a computer unit, which might also be part of an embodiment of the present invention. This computing unit may be adapted to perform or induce a performance of the steps described above. Moreover, it may be adapted to operate the components of the above-described apparatus. The computing unit can be adapted to operate automatically, and/or to execute the orders of a user. A computer program may be loaded into the working memory of a data processor. The data processor may, thus, be equipped to carry out the method of the second aspect.

This exemplary embodiment of the invention covers both a computer program which is configured to use the invention initially, or a computer program that is configured from an existing program into a program that uses the invention by means of a software update, for example.

The computer program element is thus able to provide all necessary steps necessary to fulfill the procedure required according to the second aspect discussed above.

According to a further exemplary embodiment of the present invention, a computer readable medium, such as a CD-ROM, is presented, wherein the computer readable medium has a computer readable medium has a computer program element stored on it, wherein the computer program element is described in the previous section.

A computer program may be stored and/or distributed on a suitable medium, such as an optical storage medium or a solid-state medium supplied together with, or as part of other hardware. The computer readable medium may also be distributed in other forms, such as via the internet, or other wired or wireless telecommunication systems.

The computer program can also be presented over a network like the World Wide Web, and can be downloaded into the working memory of a data processor from such a network. According to a further exemplary embodiment of aspects of the present invention, a medium for making a computer program element available for downloading is provided, which computer program element is arranged to perform a method according to one of the previously described embodiments of the invention.

It should be noted that embodiments of the invention are described with reference to different subject-matter. In particular, some embodiments are described with reference to method-type features, whereas other embodiments are described with respect to apparatus-type features. A person skilled in the art will gather from the above, and following description, that, unless otherwise notified, in addition to any combination of features belonging to one type of subject-matter, also any combination of features belonging to one type of subject-matter, also any combination between features relating to different subject-matter is considered to be disclosed within this application. All features can be combined to provide a synergetic effect, which is more than the simple summation of the features.

Whilst the invention has been illustrated and described in detail in the drawings and the foregoing description, such illustration and description are to be considered to be illustrative or exemplary, and not restrictive. The invention is not limited to the disclosed embodiments. Other variations to the disclosed embodiments can be understood, and effected, by those skilled in the art in practicing the claimed invention, from a study of the disclosure in the drawings, the description, and the dependent claims.

In the claims, the word "comprising" does not exclude other elements or steps. The indefinite article "a" or "an" does not exclude a plurality. A single processor, or other unit, may fulfill the functions of several items recited in the claims. The mere fact that certain measures are recited in mutually different dependent claims does not indicate that a combination of these measures cannot be used to advantage.

Any reference signs in the claims should not be construed as limiting the scope of the claims.

The invention claimed is:

1. A medical imaging apparatus, comprising:
   an imaging interface configured to receive medical image data from an image detector of a patient imaging arrangement including a C-arm gantry;
   an orientation information interface configured to receive orientation information of the patient imaging arrangement, wherein the orientation information comprises inclination and/or rotation signals from the patient imaging arrangement representing an inclination angle and/or a rotation angle of the C-arm gantry; and
   a processing unit configured to determine a display transformation of the medical image data based on the orientation information, to transform the medical image data from the patient imaging arrangement using the display transformation, thus providing transformed medical image data, and to output the transformed medical image data,
   wherein the orientation information interface is further configured to receive video information of a patient's alignment in the patient imaging arrangement from a video camera; and
   wherein the processing unit is further configured to process the video information to determine an offset measure of the patient from a principal patient axis relative to an alignment of the patient imaging arrangement, and to determine the display transformation based additionally on the determined offset measure.

2. The medical imaging apparatus according to claim 1, wherein the orientation information received by the orientation information interface comprises the video information of the patient imaging arrangement.

3. The medical imaging apparatus according to claim 1, further comprising:
a user interface;
wherein the user interface is further configured to receive a manual image correction signal, enabling an input of a manual image correction factor by a user; and
wherein the processing unit is further configured to determine the display transformation by combining the manual image correction factor with the orientation information.

4. The medical imaging apparatus according to claim 3, wherein the display transformation is one, or any combination of: (i) a clockwise or counter-clockwise rotation of 90 degrees, (ii) a clockwise or counter-clockwise rotation of 180 degrees, (iii), a clockwise or counter-clockwise rotation of 270 degrees, (iv) a mirror transformation applied around a horizontal and/or vertical line of symmetry, (v) an output of an orientation transfer function.

5. A method for adjusting a display orientation of a medical imaging display, comprising:
a) receiving orientation information of a patient imaging arrangement;
b) receiving medical image data from an image detector on the patient imaging arrangement;
c) determining a display transformation of the medical image data based on the orientation information;
d) transforming the medical image data from the patient imaging arrangement using the display transformation, thus providing a transformed medical image data and/or a transformed medical image sequence; and
e) displaying the transformed medical image data and/or the transformed medical image sequence,
wherein the method further comprises:
a1) receiving video information of the patient imaging arrangement from a video camera, and wherein d) further comprises:
d1) determining an offset measure of a principal patient axis, relative to an alignment of the patient imaging arrangement using the video information, and
wherein in c), the display transformation is based additionally on the determined offset of the principal patient axis relative to the alignment of the patient imaging arrangement.

6. The method of claim 5,
wherein in a), the orientation information received by an orientation information interface comprises inclination and/or rotation signals from the patient imaging arrangement.

7. The method according to claim 5, further comprising:
a2) receiving, from a user interface, a manual image correction signal, enabling a manual input of a manual image correction factor by a user; and
wherein in e), the determination of the display transformation further comprises combining the manual image correction factor with the orientation information.

8. A medical imaging system comprising:
a patient imaging arrangement;
a display unit; and
a medical imaging apparatus as claimed in claim 1;
wherein the patient imaging arrangement comprises an orientation sensor configured to provide orientation information to the medical imaging apparatus, and an image detector configured to provide medical image data to the medical imaging apparatus; and
wherein the display unit is configured to display transformed medical image data output by the medical imaging apparatus.

9. The medical imaging system according to claim 8, wherein the orientation sensor is a dual-axis or a triple axis accelerometer.

10. The medical imaging system according to claim 8, further comprising:
a video camera configured to provide video information of a location of the patient imaging arrangement to the medical imaging apparatus.

11. A non-transitory computer-readable medium having stored therein a computer program element comprising instructions for controlling a medical imaging apparatus, which, when the computer program element is executed by a control unit, is adapted to perform the method of claim 5.

* * * * *